United States Patent
Banowski et al.

(10) Patent No.: US 11,096,882 B2
(45) Date of Patent: *Aug. 24, 2021

(54) ANHYDROUS DEODORANT COMPOSITIONS WITH ABSORBER COMBINATION I

(71) Applicant: Henkel AG & Co. KGaA, Duesseldorf (DE)

(72) Inventors: Bernhard Banowski, Duesseldorf (DE); Marcus Claas, Hilden (DE); Angela Mueller, Grevenbroich (DE)

(73) Assignee: Henkel AG & Co. KGaA, Duesseldorf (DE)

(*) Notice: Subject to any disclaimer, the term of this patent is extended or adjusted under 35 U.S.C. 154(b) by 3 days.

This patent is subject to a terminal disclaimer.

(21) Appl. No.: 15/844,650

(22) Filed: Dec. 18, 2017

(65) Prior Publication Data

US 2018/0168985 A1   Jun. 21, 2018

(30) Foreign Application Priority Data

Dec. 21, 2016 (DE) ...................... 10 2016 225 736.6

(51) Int. Cl.
| | |
|---|---|
| *A61K 8/73* | (2006.01) |
| *A61K 8/25* | (2006.01) |
| *A61K 8/81* | (2006.01) |
| *A61Q 15/00* | (2006.01) |

(52) U.S. Cl.
CPC ................ *A61K 8/731* (2013.01); *A61K 8/25* (2013.01); *A61K 8/8158* (2013.01); *A61Q 15/00* (2013.01); *A61K 2800/31* (2013.01)

(58) Field of Classification Search
None
See application file for complete search history.

(56) References Cited

U.S. PATENT DOCUMENTS

| | | | |
|---|---|---|---|
| 4,743,440 | A | 5/1988 | Callingham et al. |
| 2004/0265387 | A1* | 12/2004 | Hermeling .............. A61L 15/60 424/486 |
| 2006/0140891 | A1 | 6/2006 | Nambu et al. |
| 2018/0168947 | A1 | 6/2018 | Banowski et al. |

FOREIGN PATENT DOCUMENTS

| | | |
|---|---|---|
| DE | 2453139 A1 | 5/1975 |
| DE | 2557365 A1 | 7/1977 |
| DE | 100 57 767 A1 * | 5/2002 |
| DE | 10 2008 035 014 A1 * | 1/2010 |
| DE | 102016225659 A1 | 6/2018 |
| GB | 1485373 A | 9/1977 |
| WO | 2010009977 A2 | 1/2010 |

OTHER PUBLICATIONS

English translation of DE 10 2008 035 014 A1 (2019).*
English translation of DE 100 57 767 A1 (2019).*
Intellectual Property Office, Search Report under Section 17(5) for United Kingdom Patent Application No. GB1721106.1 dated Jul. 18, 2018.

* cited by examiner

*Primary Examiner* — Patricia Duffy
*Assistant Examiner* — Garen Gotfredson
(74) *Attorney, Agent, or Firm* — Lorenz & Kopf, LLP

(57) ABSTRACT

The present disclosure relates to anhydrous cosmetic compositions which contain a combination of a strongly swelling and a low-swelling water-absorbing component, an odor-absorbing component and a deodorant active ingredient. These compositions have an outstanding deodorizing effect and improved sensory features and additionally result in a minimization of sweat spots on textiles. Furthermore, the present disclosure relates to a cosmetic product containing these anhydrous compositions and the use of this composition or product for reduction of the body odor released by perspiration. Finally, the present disclosure relates to the use of a strongly swelling water-absorbing component in combination with an odor-absorbing component to improve the sensory characteristics of anhydrous deodorant compositions.

14 Claims, No Drawings

ANHYDROUS DEODORANT COMPOSITIONS WITH ABSORBER COMBINATION I

CROSS-REFERENCE TO RELATED APPLICATION

This application claims priority to German Patent Application No. 10 2016 225 736.6, filed Dec. 21, 2016, which is incorporated herein by reference in its entirety.

TECHNICAL FIELD

The present disclosure relates to anhydrous cosmetic compositions which comprise at least one strongly swelling water-absorbing component (A), at least one low-swelling water-absorbing component (B), at least one odor-absorbing component (C) and at least one deodorant active ingredient (D). Use of the aforementioned combination in the anhydrous deodorant compositions provides a dry skin feeling and reduced formation of sweat spots on textiles, as well as an outstanding deodorizing effect.

BACKGROUND

Furthermore, the present disclosure relates to a cosmetic product comprising the aforementioned anhydrous cosmetic composition and at least one propellant (F).

The present disclosure also relates to the use of the anhydrous cosmetic composition or the cosmetic product for reduction of body odor released by perspiration.

Finally, the present disclosure relates to the use of a combination of at least one strongly swelling water-absorbing component (A) and at least one low-swelling water-absorbing component (B) and at least one odor-absorbing component (C) to improve the sensory characteristics of anhydrous deodorant compositions.

Washing, cleaning and care for the body are a basic human need and modern industry continuously attempts to meet these human needs in a variety of ways. Long-lasting elimination or at least reduction of the body odor and underarm wetness are especially important for daily hygiene. Numerous deodorizing or antiperspirant personal care products are known in the prior art, which were developed for use in body regions with a high density of sweat glands, particularly in the underarm region. They are assembled in a wide variety of dosage forms, such as a powder, stick form, aerosol spray, pump spray, liquid and gel-like roll-on application, lotion, gel and as a moist flexible substrate (deodorant wipes).

The cosmetic antiperspirants used in the prior art for reduction of perspiration contain at least an antiperspirant compound, particularly in the form of halides and/or hydroxy halides of aluminum and aluminum-zirconium. However, these compounds in combination with the acidic pH value of the agent can also cause unpleasant skin reactions with some users. Use of the aforementioned antiperspirant compounds can also cause stains on the clothing.

Therefore, there is a continued requirement for cosmetic agents which do not contain any antiperspirant aluminum and/or aluminum-zirconium salts, but also prevent formation of sweat spots on textiles. These agents should have a good, particularly dry, skin feeling, good compatibility with the skin and simple formulability, in addition to good reduction of sweat spots. Furthermore, these agents should have high storage stability.

BRIEF SUMMARY

Cosmetic compositions, cosmetic products, and methods of using the same are provided. In an exemplary embodiment, an anhydrous cosmetic composition includes at least one strongly swelling water-absorbing component (A) and at least one low-swelling water-absorbing component (B). The anhydrous cosmetic composition also includes at least one odor-absorbing component (C) and at least one deodorant active ingredient (D).

In another embodiment, a cosmetic product includes an anhydrous cosmetic composition and a propellant (F). The anhydrous cosmetic composition includes at least one strongly swelling water-absorbing component (A) and at least one low-swelling water-absorbing component (B). The anhydrous cosmetic composition also includes at least one odor-absorbing component (C) and at least one deodorant active ingredient (D).

In yet another embodiment, a method of using an anhydrous cosmetic composition includes using the anhydrous cosmetic composition to reduce body odor released by perspiration. The anhydrous cosmetic composition includes at least one strongly swelling water-absorbing component (A) and at least one low-swelling water-absorbing component (B). The anhydrous cosmetic composition also includes at least one odor-absorbing component (C) and at least one deodorant active ingredient (D).

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

The objective of the present disclosure is to provide a deodorant composition which has a good skin feeling, good compatibility with the skin, causes minimal textile soiling and has high storage stability while also reducing the formation of sweat spots on textiles.

Surprisingly, it has been found that the use of a special combination of water- and odor-absorbing components in anhydrous cosmetic deodorant compositions achieves a reduction of the formation of sweat spots on textiles and a dry skin feeling. These compositions additionally have high skin compatibility and storage stability and do not cause formation of undesired textile spots.

The subject of the present disclosure is an anhydrous cosmetic composition, containing
a) at least one strongly swelling water-absorbing component (A),
b) at least one low-swelling water-absorbing component (B)
c) at least one odor-absorbing component (C) and
d) at least one deodorant active ingredient (D).

With use of only the strongly swelling water-absorbing component (A), a high moisture absorption and thus strong reduction of the formation of sweat spots on textiles is achieved. However, as a result of the high moisture absorption, component (A) partially dissolves or swells, leaving behind a greasy film on the skin. This film is perceived as unpleasant by the consumer. Use of only component (B), by contrast, does not result in an unpleasant skin feeling, however, the water absorption capacity of this component is insufficient. Surprisingly, it has now been found that a combination of the aforementioned components (A) and (B) can achieve a high water-absorption capacity and thus a reliable minimization of textile spots and a pleasant skin feeling. Without wishing to restrict this in theory, the addition of the low-swelling water-absorbing component (B) leads to a reduction and/or avoidance of the greasy skin feeling caused by the absorption of a large quantity of water by component (A), but without negatively influencing the high moisture-absorbing capability of component (A). Therefore, the combination of absorber (A) and (B) in the anhydrous cosmetic agents of the present disclosure achieves an outstanding reduction of sweat spots on textiles and a dry skin feeling during use of this composition. In addition, the aforementioned absorber combination can be easily incorporated into existing cosmetic formulations without resulting in incompatibilities and thus a reduced storage stability. Furthermore, an improved deodorizing effect is achieved due to the minimization of the quantity of sweat, because decomposition of sweat by bacteria is reduced. This deodorizing effect is further increased with the use of the odor-absorbing component (C) and the deodorant active ingredient (D).

In the context of the present disclosure, the term "anhydrous cosmetic compositions" is understood to mean compositions which contain free water in a total quantity of from about 0 wt. % to about 1.0 wt %, preferably from about 0 to about 0.8 wt. %, more preferably from about 0 wt. % to about 0.5 wt. %, particularly from about 0 to about 0.2 wt. %, relative to the total weight of the cosmetic composition in each case. Free water within the meaning of the present disclosure is understood to mean water that is different from crystalline water, hydration water, similarly molecularly bound water or water bound on the components that are used.

Furthermore, the term "strongly swelling water-absorbing component" in the context of the present disclosure is understood to mean a compound which can absorb from about 10 to about 50 times, in particular from about 20 to about 40 times its own weight in water. The term "low-swelling water-absorbing component" is understood to mean a compound which can absorb from about 1 to about 9 times its own weight in water. The quantity of water absorbed by the respective compound can be determined, for example, by employing the method described below. A cleaning sponge (6.5 cm×5.5 cm) is drenched with about 75 g of about a 1 wt. % NaCl solution in a petri dish (diameter 11 cm) by squeezing it. Furthermore, about 50 g of the about 1 wt. % NaCl solution is added to the sponge. Then the water absorption of the black band round filter (diameter 55 mm) that is used is determined by weighing it, placing it on the drenched cleaning sponge for about 30 minutes and weighing it again after removal of the excess water from the filter by employing suctioning with a water jet pump (for about 30 seconds). The factor $F_f$ for the water absorption capacity of the filter is the result of the difference of the weight of the wet and the dry filter. The water absorption capacity of the respective compound $F_v$ is determined according to this factor, wherein about 0.2 g of this compound is distributed thinly on a dry black band filter (diameter 55 mm), about 2 g of about a 1 wt. % NaCl solution is dripped on the powder and then the filter is placed on the soaked cleaning sponge for about 30 minutes. After the excess water is removed by suctioning with a water jet pump (for about 30 seconds), the weight of the filter on which the wet compound is accumulated is determined. In the process, it must be ensured that the black band filters used to determine the water absorption capacity of the filter and the respective compound originate from the same batch. The water absorption capacity of the respective compound $F_v$ can be determined with the formula $F_v$=m(filter+wet powder)−m(powder)−m(filter)*$F_f$, wherein a 4-fold determination is carried out and then averaged for each compound.

Furthermore, the term "deodorant active ingredient" in the context of the present disclosure is understood to mean a compound which has antimicrobial and/or enzyme-inhibiting properties. This also includes compounds which can conceal the unpleasant body odor arising from the decomposition of sweat or can positively change the odor perception of body odor. However, the aforementioned compounds (A) and (B) do not fall under deodorant active ingredients. Preference is given to deodorant active ingredients that are not antiperspirant aluminum and/or aluminum zirconium salts. Therefore, preferred anhydrous cosmetic agents of the present disclosure contain about 0 wt. % antiperspirant aluminum and/or aluminum-zirconium salts, relative to the total weight of the cosmetic composition.

Finally, the term "odor-absorbing component" in the context of the present disclosure is understood to mean a component which can reversibly and/or irreversibly, preferably irreversibly, absorb liquid and/or gaseous and/or solid compounds.

The specification of wt. % presently relates to the total weight of the anhydrous cosmetic agent, unless something different is indicated.

The anhydrous cosmetic compositions contain at least one strongly swelling water-absorbing component (A) as a first essential component. In the context of the present disclosure, preference is given to use of certain compounds as component (A). Preferred embodiments of the present disclosure are exemplified in that the at least one strongly swelling water-absorbing component (A) is selected from the group of xanthan gum, gellan gum, cellulose gum, cellulose ethers, linear sodium polyacrylates, alginic acid and its salts, carrageenan and its salts, agar agar, pectins, guar gum, starch ethers, starch esters, locust bean flour, gelatins, succinoglycan, polyvinylpyrrolidone, crosslinked copolymers of acrylamide and acrylic acid, tara gum and mixtures thereof, particularly from sodium carboxymethylcellulose and/or crosslinked polymers of acrylamide and acrylic acid. Preference is given to sodium salts of alginic acid, as well as sodium, potassium, magnesium and calcium salts of carrageenan. Furthermore, use of sodium carboxymethylcellulose as cellulose ether has been proven to be useful. Examples of suitable starch esters as contemplated herein are hydroxypropyl starch phosphates and hydroxypropyl distarch phosphates. Succinoglycanes are bacterially produced polysaccharides having repeat units, each including about 7 glucose units and 1 galactose unit. Tara gum (also referred to as *caesalpinia spinosa* gum) can be obtained by grinding the seeds of the plant *caesalpinia spinosa*. Particular preference is given to sodium carboxymethyl cellulose (commercially available, for example, under the trade name Cekol 30000 from the company CP Kelco) and/or crosslinked copolymers of acrylamide and acrylic acid (commercially available, for example, under the trade name Aquasorb A 100 from the company Ashland) as the strongly swelling water-absorbing components (A). Use of the aforementioned component (A), particularly sodium carboxymethyl cellulose, achieves an especially good reduction of sweat spots on textiles due to the high moisture absorption capability.

As contemplated herein, it has been found that use of the component (A) in powder form with a certain average particle size is advantageous. Therefore, as contemplated herein, it is preferred if at least one strongly swelling water-absorbing component (A) is present in particle form, wherein at least about 30 wt. % of component (A) has an average particle size $D_{50}$ of more than about 10 μm and wherein about 100 wt. % of component (A) has an average particle size $D_{50}$ of less than about 200 μm. The wt % specification is relative to the total weight of component (A). The average particle size $D_{50}$ can, for example, be determined by employing dynamic light scattering (DLS). Use of component (A) with the aforementioned average particle sizes results in an especially good moisture absorption, but without negatively influencing the storage stability.

In the context of the present disclosure, preference is given use of component (A) in specific quantity ranges. Therefore, it is advantageous if the at least one strongly swelling water-absorbing component (A), particularly sodium carboxymethylcellulose and/or crosslinked copolymers of acrylamide and acrylic acid, is included in a total quantity of from about 1.0 to about 40 wt. %, preferably from about 1.5 to about 30 wt. %, more preferably from about 2.0 to about 20 wt. %, particularly from about 3.0 to about 15 wt. %, relative to the total weight of the anhydrous cosmetic composition. The aforementioned quantity specifications relate to the total quantity of component (A). If only one compound is used as component (A), these quantity specifications are relative to the total amount of the individual compound. If, by contrast, a mixture of different components (A) is used, the aforementioned quantity specifications relate to the total amount of the mixture of different components (A). Use of the aforementioned total amounts achieves especially high moisture absorption and thus outstanding reduction of sweat spots on textiles. On the other hand, the problem addressed by the additional use of the component (B) does not adversely affect the dry skin feeling achieved even when high quantities of moisture are absorbed by the component (A). In addition, when using the aforementioned total quantities, no negative influence on the storage stability of the cosmetic composition as contemplated herein occurs.

The water-absorbing cosmetic compositions as contemplated herein contain at least one low-swelling water-absorbing component (B) as the second essential component. Preference is given to use of certain compounds as component (B). Therefore, in the context of the present disclosure, it is advantageous if the at least one low-swelling water-absorbing component (B) is selected from the group of celluloses, silica, modified silica and mixtures thereof, particularly hydrophilic silica and/or cellulose. However, the aforementioned celluloses and microcrystalline celluloses do not include the cellulose gums mentioned in connection with component (A). For example, modified silica can be obtained by employing surface modification using various chemical compounds. In the context of the present disclosure, preference is given to use of hydrophilic silica having a BET surface area of from about 250 to about 350 m²/g (commercially available, for example, under the trade name Aeropearl® 300/30 from the company Evonik) and/or cellulose (commercially available, for example, under the name Sensocel OC 30 g from the company CFF) as low-swelling water-absorbing components (B). Use of the aforementioned components (B), particularly hydrophilic silica with a BET surface of from about 250 to about 350 m²/g and/or cellulose, prevents formation of a greasy film by component (A) and achieves a dry skin feeling. The high moisture absorption capability of component (A) is not negatively influenced in this connection, so a good reduction of sweat spots on textiles is achieved.

As contemplated herein, it has been found that use of the component (B) in powder form with a certain average particle size is also advantageous. Therefore, preferred embodiments of the present disclosure are exemplified in that the at least one low-swelling water-absorbing component (B) is present in particle form, wherein at least about 30 wt. % of component (B) has an average particle size $D_{50}$ of more than about 10 μm and wherein about 100 wt. % of component (B) has an average particle size $D_{50}$ of less than about 200 μm. The wt. % specification is relative to the total weight of component (B). The average particle size $D_{50}$ can, for example, be determined by employing dynamic light scattering (DLS). Use of component (B) with the aforementioned average particle sizes results in an especially dry skin feeling, but without negatively influencing the moisture absorption capability of component (A).

In the context of the present disclosure, preference is given use of component (B) in specific quantity ranges. Therefore, it is advantageous if the at least one low-swelling water-absorbing component (B), particularly hydrophilic silica and/or cellulose, is included in a total quantity of from about 1.0 to about 40 wt. %, preferably from about 1.5 to about 30 wt. %, more preferably from about 2.0 to about 20 wt. %, particularly from about 2.0 to about 15 wt. %, relative to the total weight of the anhydrous cosmetic composition. The aforementioned quantity specifications relate to the total quantity of component (B). If only one compound is used as component (B), these quantity specifications are relative to the total amount of the individual compound. If, by contrast, a mixture of different components (B) is used, the aforementioned quantity specifications relate to the total amount of the mixture of different components (B). Use of the aforementioned total quantities results in especially dry skin feeling, even with absorption of high quantities of moisture by component (A). In addition, when using the aforementioned total quantities, no negative influence on the moisture absorption capacity of component (A) and the storage stability of the cosmetic composition as contemplated herein occurs.

Preferred embodiments of the present disclosure contain a specific weight ratio of component (A) to component (B). Use of such weight ratios has been demonstrated to be especially advantageous in regard to moisture absorption and reduction of sweat spots on textiles while achieving a dry skin feeling. As contemplated herein, therefore, it is preferred if the anhydrous cosmetic composition has a weight ratio of the at least one strongly swelling water-absorbing component (A) to the at least one low-swelling water-absorbing component (B) of from about 8:2 to about 2:8, preferably of from about 7:2 to about 2:7, particularly of from about 7:3 to about 4:6. In this connection, the weight ratios relate to the respective total quantities of component (A) and component (B).

As a third essential component, the anhydrous cosmetic composition contains at least one odor-absorbing component (C), which is different from components (A) and (B). Preference is given to use of certain compounds as component (C). Therefore, in the context of the present disclosure, it is advantageous if the at least one odor-absorbing component (C) is selected from the group of (i) cyclodextrins and derivatives thereof; (ii) crosslinked polyacrylates; (iii) polyethylenes and nylon; (iv) zeolites, in particular ammonium silver zeolite, silver copper zeolite and zinc zeolite; (v) bischloride(-1)-octahydroxy-pentazinc; (vi) metal carbonates and metal bicarbonates, in particular zinc carbonate, magnesium carbonate and sodium bicarbonate; (vii) metal hydroxides, in particular magnesium hydroxide, zinc hydroxide and zinc chloride hydroxide; (viii) metal oxides, in particular aluminum oxide, magnesium oxide and zinc oxide; (ix) diatoms, (x) metal oxide hydroxides, metal oxide carbonates and metal hydroxide carbonates, in particular zinc carbonate hydroxide; (xi) silicates and aluminates, in particular sodium aluminum silicates, aluminum silicates, ammonium/silver-zinc aluminum silicates, calcium magnesium silicates, calcium silicate, magnesium aluminum metasilicate, magnesium aluminum silicate, magnesium silicate, magnesium trisilicate, sodium silver aluminum silicate and sodium silicoaluminate; (xii) starches and derivatives thereof, in particular aluminum and sodium salts of starch esterified with octenylsuccinic anhydride, modified maize starch, glyceryl starch, amylopectin, maltodextrin, dimethylimidazolidone-modified starch; (xiii) zinc ricinoleate; (xiv) activated carbon and derivatives thereof; (xv) zinc salts of the L-pyrrolidone carboxylate; (xvi) minerals and rocks, in particular bentonites, silica, hectorite, kaolin, montmorillonite, perlite, talcum, pyroclasts and silt; (xvii) dendrimers, in particular dendrimers formed from the reaction of ethoxylated pentaerythritol with dimethylpropionic acid; (xviii) isolated plant constituents, in particular cotton powder, wood powder and bamusa arundiacea stem extract; (xix) metal powders, in particular noble metal powders; (xx) protein powders; (xxi) metal-organic frameworks (MOFs) from polyvalent metal ions and multivalent aromatic acids; (xxii) microcrystalline celluloses; and mixtures thereof. In the scope of the present disclosure, derivatives of active carbons are understood to mean active carbons which were modified by employing chemical and/or physical methods. Furthermore, diatoms are understood to mean single-cell algae having a cell wall predominantly including silicon dioxide. Furthermore, starch derivatives are understood to mean starches which were modified by employing chemical reactions or hydrolyzed by employing enzymes. The aforementioned isolated plant components can also be ground and used in the form of a powder. Particularly preferred odor-absorbing components (C) are selected from the group of cyclodextrines and their derivatives, zeolites, sodium hydrogen carbonate, magnesium hydroxide, magnesium carbonate, magnesium oxide, zinc carbonate, zinc carbonate hydroxide, silica, sodium aluminum silicates, zinc ricinoleate, zinc salts of the L-pyrrolidone carboxylate, sodium silicoaluminates, magnesium calcium silicates, magnesium aluminum silicates, zinc chloride hydroxide, noble metal powders, perlites, metal-organic frameworks (MOFs) and mixtures thereof. By additionally using the aforementioned odor-absorbing component (C), the deodorizing effect and the dry skin feeling of the compositions are further enhanced.

As contemplated herein, it has been found that use of the component (C) in powder form with a certain average particle size is also advantageous. Therefore, preferred embodiments of the present disclosure are exemplified in that the at least one odor-absorbing component (C) is present in particle form, wherein at least about 20 wt. % of component (C) has an average particle size $D_{50}$ of more than about 10 μm and wherein about 100 wt. % of component (C) has an average particle size $D_{50}$ of less than about 200 μm. The wt % specification is relative to the total weight of component (C). The average particle size $D_{50}$ can, for example, be determined by employing dynamic light scattering (DLS). Use of component (C) with the aforementioned average particle sizes achieves a particularly good improvement of the deodorizing effect of the composition.

In the context of the present disclosure, preference is given use of component (B) in specific quantity ranges. Therefore, it is advantageous if the at least one odor-absorbing component (C) is included in a total quantity of from about 0.2 to about 40 wt. %, preferably from about 1.0 to about 30 wt. %, more preferably from about 2.0 to about 20 wt. %, particularly from about 2.0 to about 15 wt. %, relative to the total weight of the anhydrous cosmetic composition. The aforementioned quantity specifications relate to the total quantity of component (C). If only one compound is used as component (C), these quantity specifications are relative to the total amount of the individual compound. If, by contrast, a mixture of different components (C) are used, the aforementioned quantity specifications relate to the total amount of the mixture of different components (C). Use of the aforementioned total quantities has an especially high improvement of the deodorizing effect and the dry skin feeling of the composition. In addition, when using the aforementioned total quantities, no negative influence on the moisture absorption capacity of components (A) and (B) and the storage stability of the cosmetic composition as contemplated herein occurs.

The anhydrous cosmetic composition contains at least one deodorant active ingredient (D) as a fourth essential component. This deodorant active ingredient (D) differs from the components (A) to (C). Use of certain deodorant active ingredients has been demonstrated to be beneficial as contemplated herein. Therefore, in the context of the present disclosure, it is preferable if the at least one deodorant active ingredient (D) is selected from the group of (i) arylsulfatase inhibitors, beta-glucuronidase inhibitors, aminoacylase inhibitors, esterase inhibitors, lipase inhibitors and lipoxygenase inhibitors; (ii) α-monoalkyl glycerol ethers having a branched or linear saturated or unsaturated, optionally hydroxylated $C_6$-$C_{22}$-alkyl radical, in particular α-(2-ethylhexyl) glycerol ethers, (iii) alcohols, in particular phenoxyethanol, benzyl heptanol, 1,2-hexanediol, 1,2-octanediol, 1,2-decanediol, tropolone and butyloctanoic acid; (iv) germ-inhibiting perfume oils; (v) prebiotically active components; (vi) trialkyl citric acid esters, in particular triethyl citrate; (vii) active substances which influence the number of skin germs from the group of staphylococci involved in the odor formation, coryneform bacteria, anaerococci and micrococci or inhibit their growth; (viii) zinc and silver compounds, in particular zinc phenolsulfonate, bischloride(-1)-octahydroxy-pentazinc, zinc citrate and silver lactate; (ix) organohalogen compounds, in particular triclosan, chlorhexidine and chlorhexidine gluconate; (x) benzalkonium halides, in particular benzalkonium chloride and benzethonium chloride; (vi) quaternary ammonium compounds, in particular cetylpyridinium chloride; (xii) antimicrobially active carbonates, phosphates and sulfates, in particular sodium bicarbonate, cocamidopropyl PG-dimonium chloride phosphate, disodium pyrophosphate and soya morpholinium ethosulfate; (xiii) Lantibiotics; (xiv) aluminum and aluminum zirconium salts; (xv) bispyridines, in particular octenidine; (xvi) antimicrobially active acids, in particular caprylic hydroxamic acid, camesol acid and tartaric acid; (xvii) polyglycerol esters; (xviii) sorbitan esters and lactones, in particular sorbitan caprylate and glucono-1,5-lactone; (xix) and mixtures thereof, in particular phenoxyethanol and/or caprylyl glycol and/or 1,2-hexanediol and/or α-(2-ethylhexyl) glycerol ether. Especially good results in regard to the deodorizing effect are achieved in the context of the present disclosure if the at least one deodorant active ingredient (D) is selected from phenoxyethanol and/or caprylyl glycol and/or 1,2-hexanediol and/or α-(2-ethylhexyl) glycerol ether and/or benzyl heptanol and/or butyloctanoic acid. Therefore, this preferred embodiment contains only the aforementioned compounds in the form of phenoxyethanol and/or caprylyl glycol and/or 1,2-hexanediol and/or α-(2-ethylhexyl) glycerol ether and/or benzyl heptanol and/or butyloctanoic acid as the deodorant active ingredient (D), but does not contain any antiperspirant aluminum and aluminum-zirconium salts.

It is preferable if the at least one deodorant active ingredient (D), particularly the aforementioned particularly preferred deodorant active ingredients, is used in a specific total amount. In this connection, the term total amount is understood to mean the sum of the quantities of all deodorant active ingredients. Therefore, if a mixture of different deodorant active ingredients (D) is used, the following quantity specifications relate to the total amount of the mixture of deodorant active ingredients. Therefore, preferred embodiments of the present disclosure are exemplified in that the at least one deodorant active ingredient (D) is contained in a total quantity of from about 0.0001 to about 15 wt. %, preferably from about 0.001 to about 15 wt. %, more preferably from about 0.01 to about 15 wt. %, and most preferably from about 0.5 to about 15 wt. %, relative to the total weight of the anhydrous cosmetic composition. Use of the at least one deodorant active ingredient, particularly phenoxyl ethanol and/or caprylyl glycol and/or 1,2-hexanediol and/or α-(2-ethylhexyl)glycerol and/or benzyl heptanol and/or butyloctanoic acid in the aforementioned total amount achieves an especially good and long-lasting deodorizing effect of the anhydrous cosmetic composition.

The anhydrous cosmetic composition can contain further ingredients, in addition to the aforementioned essential components (A) to (D). The aforementioned components (A) to (C), as well as the deodorant active ingredient (D) are preferably contained in an anhydrous cosmetic carrier. Such carriers are, for example, cosmetic oils. This is understood to include oils that are suitable for cosmetic use, which are not miscible in all quantities. However, such oils do not include fragrances and essential oils. Therefore, in the context of the present disclosure, it is preferred if the anhydrous cosmetic composition additionally contains at least one cosmetic oil (E), selected from the group of (i) volatile cyclic silicone oils, particularly cyclotrisiloxane, cyclotetrasiloxane, cyclopentadienyl and cyclohexasiloxane, and linear silicone oils having from about 2 to about 10 siloxane units, in particular hexamethyldisiloxane, octamethyltrisiloxane, decamethyltetrasiloxane; (ii) volatile non-silicone oils, in particular liquid paraffin oils and isoparaffin oils, such as isodecane, isoundecane, isododecane, isotridecane, isotetradecane, isopentadecane, isohexadecane and isoeicosane; (iii) non-volatile silicone oils, in particular higher molecular weight linear polyalkylsiloxanes; (iv) non-volatile non-silicone oils, in particular the esters of linear or branched saturated or unsaturated $C_{2-30}$-fatty alcohols with linear or branched saturated or unsaturated $C_{2-30}$-fatty acids, which can be hydroxylated, the $C_8$-$C_{22}$-fatty alcohol esters of monohydric or polyhydric $C_2$-$C_7$-hydroxycarboxylic acids, the triethyl citrates, the branched saturated or unsaturated $C_{6-30}$-fatty alcohols, the mono-, di- and triglycerides of linear or branched, saturated or unsaturated, optionally hydroxylated $C_{8-30}$-fatty acids, the dicarboxylic acid esters of linear or branched $C_2$-$C_{10}$-alkanols, the addition products of ethylene oxide and/or propylene oxide onto mono- or multivalent $C_{3,22}$-alkanols, which may optionally be esterified, the symmetrical, asymmetric or cyclic esters of carbonic acid with fatty alcohols, the esters of dimeric unsaturated $C_{12-22}$-fatty acids with monohydric, linear, branched and cyclic $C_{2-18}$-alkanols or $C_{2-6}$-alkanols, the benzoic esters of linear or branched $C_{8-22}$-alkanols, such as the benzoic acid $C_{12-15}$-alkyl ester and the benzoic acid isostearyl ester and the benzoic acid octyldodecyl ester, synthetic hydrocarbons, such as polyisobutene and polydecenes, the alicyclic hydrocarbons; and (v) mixtures thereof. The term "fatty acids" is understood to mean aliphatic carboxylic acids which have unbranched or branched carbon radicals with 4 to 40 carbon atoms. These can be both naturally occurring and synthetically produced fatty acids. Furthermore, the fatty acids can be mono- or polyunsaturated. The term "fatty alcohols" is understood to mean aliphatic, monovalent, primary alcohols, which have unbranched or branched hydrocarbon radicals having from about 4 to about 40 carbon atoms and can be mono- or polyunsaturated. The term "liquid cosmetic oil" refers to cosmetic oils as contemplated herein which have a vapor pressure of from about 2.66 Pa to about 40,000 Pa (from about 0.02 to about 300 mm Hg), preferably from about 10 to about 12,000 Pa (from about 0.1 to about 90 mm Hg), more preferably from about 13 to about 3,000 Pa (from about 0.1 to about 23 mm Hg), particularly from about 15 to about 500 Pa (from about 0.1 to about 4 mm Hg) at 20° C. and an environmental pressure of about 1.013 hPa. By contrast, the term "non-liquid cosmetic oils" within the context of the present disclosure is understood to mean cosmetic oils that have a vapor pressure of less than about 2.66 Pa (0.02 mm Hg) at about 20° C. and an environmental pressure of about 1,013 hPa.

As a result of the use of a mixture of volatile silicone oils and volatile non-silicone oils, the liquid silicone oil produced by the component (B) can be increased further. In order to mask insoluble constituents, such as talc or the absorber combination used, it can be preferred, if the cosmetic compositions as contemplated herein contain a non-volatile silicone oil and/or a non-volatile non-silicone oil. It can also be provided that the cosmetic compositions as contemplated herein contain a mixture of volatile and non-volatile cosmetic oils, because in this way parameters such as the skin feel and stability of the cosmetic agent as contemplated herein can be further optimized and adapted to the requirements of the consumers.

In this context, it has been demonstrated to be advantageous if the at least one cosmetic oil (E) is selected from cyclopentadienyl, polydimethylsiloxane having a kinematic viscosity of 2 to 30 cSt, ethylhexyl palmitate, isopropyl myristate and mixtures thereof. Particular preference is given to use of mixtures of cyclopentadienyl, ethylhexyl palmitate and isopropyl myristate or polydimethylsiloxane having a kinematic viscosity of from about 2 to about 30 cSt as cosmetic oil (E), because the dry skin feeling of the composition achieved by the component (B) can be further improved as a result.

The at least one cosmetic oil (E) is preferably used in certain quantity ranges. Preferred embodiments of the present disclosure are exemplified in that the at least one cosmetic oil (E) is contained in a total quantity of from about 1.0 to about 95 wt. %, preferably from about 10 to about 85 wt. %, more preferably from about 20 to about 80 wt. %, and particularly from about 30 to about 80 wt. %, relative to the total weight of the anhydrous cosmetic composition. If a mixture of different cosmetic oils (E) mentioned above, particularly a mixture of cyclomethicone, ethylhexyl palmitate, isopropyl myristate and polydimethylsiloxane having a kinematic viscosity of from about 2 to about 30 cSt, the aforementioned quantity specifications relate to the total amount of the mixture of cosmetic oils (E). If, by contrast, only one of the aforementioned compounds (E) is used, these quantity specifications relate to the total amount of the one compound (E). In the context of the present disclosure, use of a total amount of from about 75 to about 80 wt. %, relative to the total weight of the composition, of a mixture of cyclomethicone, ethylhexyl palmitate, isopropyl myristate or polydimethylsiloxane having a kinematic viscosity of from about 2 to about 30 cSt in a weight ratio of from about 12:7:1 to about 8:4:1 has been demonstrated to be advantageous in regard to the dry skin feeling.

Furthermore, the cosmetic composition can contain additional ingredients. These ingredients are preferably selected from the group of (i) fragrances; (ii) waxes; (iii) emulsifiers and/or surfactants; (iv), chelating agents; (v) polyethylene glycols; (vi) skin-cooling active ingredients; (vii) pH control agents; (viii) skin-care active ingredients, such as moisturizers, skin-calming substances, skin-lightening substances, skin-smoothing substances; (ix) preservatives; and (x) mixtures thereof.

Preferred embodiments of the present disclosure contain at least one fragrance, in addition to the aforementioned mandatory components (A) to (D). As contemplated herein, this is understood to mean substances having a molar mass of from about 74 to about 300 g/mol, which contain at least one osmotic group in the molecule and have an odor and/or taste, i.e. they are capable of exciting the receptors of the hair cells of the olfactory system. Osmotic groups are groups bound covalently to the molecular structure in the form of hydroxyl groups, formyl groups, oxo groups, alkoxycarbonyl groups, nitrile groups, nitro groups, azide groups, etc. in this context, the term "fragrances" in the context of the present disclosure also comprises perfume oils which are liquid at 20° C. and 1.013 hPa, perfumes, or perfume oil constituents. Fragrances that can be used within the scope of the present disclosure are, for example, (i) esters, in particular benzyl acetate, phenoxyethyl isobutyrate, p-tert.-butylcyclohexyl acetate, linalyl acetate, dimethylbenzylcarbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate and jasmecyclate; (ii) ethers, in particular benzyl ethyl ether and ambroxol; (iii) aldehydes, in particular linear alkanals having from about 8 to about 18 carbon atoms, citral, citronellal, citronellyloxyacetaldehyde, cyclamen aldehyde, lilial and bourgeonal; (iv) ketones, in particular ionones, alpha-isomethylionone and methyl cedryl ketone; (v) alcohols, in particular anethol, citronellol, eugenol, geraniol, linalool, phenylethyl alcohol and terpineol; (vi) hydrocarbons, in particular terpenes such as limonene and pinene; and (vii) mixtures thereof. However, mixtures of different fragrances which produce a pleasant scent together are preferred.

Particularly appealing cosmetic compositions as contemplated herein are obtained if the fragrance is present in a total amount of from about 0.00001 to about 10 wt. %, preferably from about 0.001 to about 9.0 wt. %, more preferably from about 0.01 to about 8.0 wt. %, more preferably from about 0.5 to about 7.0 wt. %, particularly from about 1 to about 6.0 wt. %, relative to the total weight of the anhydrous cosmetic composition.

The compositions can contain at least one wax as an additive. These are substances which can be kneaded at 20° C. or are hard to brittle, have a coarse to fine-crystalline structure and are colored translucent to opaque, but not glass-like. These substances also melt at temperatures above 25° C. without breaking down, are only slightly fluid above the melting point (less viscous), have a consistency and solubility that are highly temperature-independent and are polishable under light pressure. Waxes which can be used in the context of the present disclosure are, for example, (i) coconut fatty acid glycerol mono-, -di-and-triesters; (ii) *Butyrospermum parkii* (shea butter); (iii) esters of saturated, monohydric $C_{8-18}$-alcohols with saturated $C_{12-18}$-monocarboxylic acids; (iv) linear, primary $C_{12}$-$C_{24}$-alkanols; (v) esters of a saturated, monohydric $C_{16}$-$C_{60}$-alkanol and a saturated $C_8$-$C_{36}$-monocarboxylic acid, in particular cetyl behenate, stearyl behenate and $C_{12}$-$C_{30}$-alkyl stearate; (vi) glycerol triesters of saturated linear $C_{12}$-$C_{30}$ carboxylic acids which can be hydroxylated, in particular hydrogenated palm oil, hydrogenated coconut oil, hydrogenated castor oil, glyceryl tribehenate and glyceryl tri-12-hydroxystearate; (vii) natural vegetable waxes, in particular candelilla wax, camauba wax, japan wax, sugar cane wax, ouricury wax, cork wax, sunflower wax, fruit waxes; (viii) animal waxes, in particular beeswax, shellac wax and spermaceti; (ix) synthetic waxes, in particular montan ester waxes, hydrogenated jojoba waxes and sasol waxes, polyalkylene waxes and polyethylene glycol waxes, $C_{20}$-$C_{40}$-dialkyl esters of dimer acids, $C_{30-50}$-alkyl beeswax and alkyl and alkylaryl esters of dimer fatty acids, paraffin waxes; and (x) mixtures thereof.

In the context of the present disclosure, it is preferred if the wax is present in a total amount of from about 0.01 to about 20 wt. %, preferably from about 3.0 to about 20 wt. %, more preferably from about 5.0 to about 18 wt. %, particularly from about 6.0 to about 15 wt. %, relative to the total weight of the anhydrous cosmetic composition.

As contemplated herein, suitable emulsifiers and surfactants are preferably selected from anionic, cationic, nonionic, amphoteric, particularly ampholytic and zwitterionic emulsifiers and surfactants. Surfactants are amphiphilic (bi-functional) compounds that include at least one hydrophobe and at least one hydrophile molecular part. The hydrophobic radical is preferably a hydrocarbon chain with from about 8 to about 28 carbon atoms, which can be saturated or unsaturated, linear or branched. It is especially preferable if this $C_8$-$C_{28}$ alkyl chain is linear.

Anionic surfactants are understood to mean surfactants having exclusively anionic charges; they contain, for example, carboxyl groups, sulfonic acid groups or sulfate groups. Particularly preferred anionic surfactants are alkyl sulfates, alkyl ether sulfates, acylglutamates and $C_{8-24}$-carboxylic acids and salts thereof, so-called soaps.

Cationic surfactants are understood to mean surfactants having exclusively cationic charges; they contain, for example, quaternary ammonium groups. Preference is given to cationic surfactants of the type of quaternary ammonium compounds, esterquats and amidoamines. Preferred quaternary ammonium compounds are ammonium halides and the imidazolium compounds known under the INCI designations quaternium-27 and quaternium-83. As contemplated herein, the quaternized protein hydrolysates can also be used. Preferred esterquats are quaternated ester salts of fatty acids with triethanolamine, quaternated ester salts of fatty acids with diethanolalkyl amines and quaternated ester salts of fatty acids with 1,2-dihydroxypropyldialkylamines.

The amphoteric surfactants are divided into ampholytic surfactants and zwitterionic surfactants. Ampholytic surfactants are surface active compounds that contain both acid (for example, —COOH or —SO$_3$H groups) and also alkaline hydrophilic groups (for example, amino groups) and have acidic or alkaline behavior depending on the condition. Zwitterionic surfactants are specialist surfactants that carry both a negative and a positive charge in the same molecule. Examples of preferred zwitterionic surfactants are betaines, the N-alkyl-N, N-dimethylammoniumglycinates, N-acylaminopropyl-N, N-dimethylammoniumglycinate and the 2-alkyl-3-carboxymethyl-3-hydroxyethyl-imidazolines, each having from about 8 to about 24 carbon atoms in the alkyl group. Examples of preferred ampholytic surfactants are N-alkylglycines, N-alkylaminopropionic acids, N-alkylaminobutyric acids, N-alkyliminodipropionic acids, N-hydroxyethyl-n-alkylamidopropyl-glycines, N-alkyl taurines, N-alkyl sarcosines, 2-alkylaminopropionic acids and alkylaminoacetic acids having from about 8 to about 24 carbon atoms in the alkyl group in each case.

Examples of preferred nonionic surfactants which have no charged or ionizable groups are (i) linear saturated alcohols having from about 12 to about 30 carbon atoms, (ii) esters and partial esters of a polyol having from about 3 to about 6 carbon atoms and linear saturated and unsaturated fatty acids having from about 12 to about 30 carbon atoms, which can be hydroxylated, (iii) sterols and ethoxylated sterols, (iv) alkanols and carboxylic acids having in each case from about 8 to about 24 carbon atoms and on average from about 1 to about 100 ethylene oxide units per molecule, (v) glycerol monoethers of saturated and/or unsaturated, branched and/or unbranched alcohols having a chain length of from about 8 to about 30 carbon atoms, (vi) partial esters of polyglycerols having from about 2 to about 10 glycerol units, which are saturated or unsaturated with from about 1 to about 5 saturated or unsaturated, linear or branched carboxylic acids having from about 8 to about 30 carbon atoms, which can be hydroxylated, (vii) silicone copolyols with ethylene oxide units or with ethylene oxide and propylene oxide units, (viii) alkyl mono- and oligoglycosides having from about 8 to about 22 carbon atoms in the alkyl radical and their ethoxylated analogs and (ix) mixtures thereof.

In the context of the present disclosure, preferred chelating agents are selected from the group of beta-alaninediacetic acid, cyclodextrin, diethylene triamine pentamethylene phosphonic acid, sodium, potassium, calcium disodium, and calcium-, ammonium and triethanolamine salts of ethylenediaminetetraacetic acid (EDTA), etidronic acid, hydroxyethylethylenediaminetetraacetic acid (HEDT) and sodium salts thereof, sodium salts of nitrilotriacetic acid (NTA), diethylene triamine pentaacetic acid, phytic acid, hydroxypropyl cyclodextrin, methylcyclodextrin, aminotrimethylene phosphonate pentasodium, ethylenediamine tetramethylene phosphonate pentasodium, diethylene triamine pentaacetate pentasodium, pentasodium triphosphate, potassium EDTMP, sodium EDTMP, sodium dihydroxyethylglycinate, sodium phytate, sodium polydimethylglycinylphenol sulfonate, tetrahydroxyethyl ethylenediamine, tetrahydroxypropyl ethylenediamine, tetrasodium iminodisuccinate, trisodium ethylenediamine disuccinate, tetrasodium-n, n-bis(carboxymethyl)glutamate, tetrasodium DL-alanine-n, n-diacetate and desferrioxamine. These chelating agents are advantageously present in a total amount of from about 0.01 to about 3.0 wt. %, preferably from about 0.02 to about 1.0 wt. %, in particular from about 0.05 to about 0.3 wt. %, relative to the total weight of the anhydrous cosmetic composition. It has been demonstrated that the use of such chelating agents results in an increase of the deodorizing effect of component (C).

Furthermore, preferred antiperspirant cosmetic agents as contemplated herein contain at least one water-soluble polyvalent $C_{2-9}$-alkanol with from about 2 to about 6 hydroxyl groups and/or at least one water-soluble polyethylene glycol with from about 3 to about 50 ethylene oxide units and mixtures thereof. However, this does not include the aforementioned deodorant active ingredients in the form of 1,2-alkane diols. Suitable polyethylene glycols are selected from PEG-3, PEG-4, PEG-6, PEG-7, PEG-8, PEG-9, PEG-10, PEG-12, PEG-14, PEG-16, PEG-18 and PEG-20 and mixtures thereof, such as PEG-3 to PEG-8 are preferred.

According to a further embodiment of the present disclosure, the antiperspirant cosmetic compositions additionally comprise at least one skin-cooling active ingredient. Suitable skin-cooling active ingredients as contemplated herein are, for example, menthol, isopulegol and menthol derivatives, such as menthyl lactate, menthyl glycolate, menthyl ethyl oxamates, menthyl pyrrolidone carboxylic acid, menthyl methyl ether, menthoxypropane diol, menthoxyglycerol acetal (9-methyl-6-(1-methylethyl)-1,4-dioxaspiro (4.5) decane-2-methanol), monomenthyl succinate, 2-hydroxymethyl-3,5,5-trimethylcyclohexanol and 5-methyl-2-(1-methylethyl) cyclohexyl-n-ethyl oxamate. Menthol, isopulegol, menthyl lactate, menthoxypropane diol, menthyl pyrrolidone carboxylic acid and 5-methyl-2-(1-methylethyl) cyclohexyl-n-ethyl oxamate and mixtures of these substances, in particular mixtures of menthol and menthyl lactate, menthol, menthol glycolate and menthyl lactate, menthol and menthoxypropanediol or menthol and isopulegol, are preferred as skin-cooling active ingredients.

As contemplated herein, acids and/or alkalizing agents and/or buffers are preferred for use as pH control agents. As contemplated herein, inorganic acids are preferred for use as acids (such as hydrochloric acid, sulfuric acid or phosphoric acid) or organic acids (such as citric acid, tartaric acid or malic acid). The alkalizing agents that can be used as contemplated herein are preferably selected from the group comprising ammonia, basic amino acids, carbonates and hydrogen carbonates, alkanolamines, for example amino-2-methyl-1-propanol, monoethanolamine, triethanolamine, diethanolamine and triisopropanolamine, alkali metal metasilicates, urea, morpholine, N-methylglucamine and imidazole, alkali phosphates and alkali hydrogen phosphates. Lithium, sodium and potassium, particularly sodium or potassium are preferred for use as alkali metal ions. Carbonic acid bicarbonate buffer, carbonic acid silicate buffer, acetic acid acetate buffer, phosphate buffer, ammonia buffer, citric acid or citrate buffer, buffer based on tris(hydroxymethyl)-aminomethane, buffer based on 4-(2-hydroxyethyl)-1-piperazineethanesulfonic acid, buffer based on 4-(2-hydroxyethyl)-piperazine-1-propanesulfonic acid, buffer based on 2-(n-morpholino)ethanesulfonic acid and barbital acetate buffer, in particular, are suitable as buffer systems in the context of the present disclosure. Selection of the appropriate buffer system is determined on the basis of the desired pH value of the antiperspirant cosmetic agent.

Particularly preferred embodiments AF1 to AF108 of the anhydrous composition as contemplated herein are described below (all specifications in wt. %). All compositions below have a total amount of free water of from about 0 to about 1.0 wt. %, particularly from about 0 to about 0.2 wt. %, relative to the total weight of the respective embodiment.

|  | AF 1 | AF 2 | AF 3 | AF 4 |
| --- | --- | --- | --- | --- |
| Water-absorbing component (A) | 1.0-40 | 1.5-30 | 2.0-20 | 3.0-15 |
| Water-absorbing component (B) | 1.0-40 | 1.5-30 | 2.0-20 | 2.0-15 |
| Odor-absorbing component (C) | 1.0-40 | 1.5-30 | 2.0-20 | 2.0-15 |

-continued

| | | | | |
|---|---|---|---|---|
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

| | AF 5 | AF 6 | AF 7 | AF 8 |
|---|---|---|---|---|
| Water-absorbing component (A)[1] | 1.0-40 | 1.5-30 | 2.0-20 | 3.0-15 |
| Water-absorbing component (B) | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

| | AF 9 | AF 10 | AF 11 | AF 12 |
|---|---|---|---|---|
| Water-absorbing component (A)[2] | 1.0-40 | 1.5-30 | 2.0-20 | 3.0-15 |
| Water-absorbing component (B) | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

| | AF 13 | AF 14 | AF 15 | AF 16 |
|---|---|---|---|---|
| Water-absorbing component (A)[3] | 1.0-40 | 1.5-30 | 2.0-20 | 3.0-15 |
| Water-absorbing component (B) | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

| | AF 17 | AF 18 | AF 19 | AF 20 |
|---|---|---|---|---|
| Water-absorbing component (A) | 1.0-40 | 1.5-30 | 2.0-20 | 3.0-15 |
| Water-absorbing component (B)[4] | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

| | AF 21 | AF 22 | AF 23 | AF 24 |
|---|---|---|---|---|
| Water-absorbing component (A) | 1.0-40 | 1.5-30 | 2.0-20 | 3.0-15 |
| Water-absorbing component (B)[5] | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

| | AF 25 | AF 26 | AF 27 | AF 28 |
|---|---|---|---|---|
| Water-absorbing component (A) | 1.0-40 | 1.5-30 | 2.0-20 | 3.0-15 |
| Water-absorbing component (B)[6] | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

| | AF 29 | AF 30 | AF 31 | AF 32 |
|---|---|---|---|---|
| Water-absorbing component (A) | 1.0-40 | 1.5-30 | 2.0-20 | 3.0-15 |
| Water-absorbing component (B) | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

| | AF 33 | AF 34 | AF 35 | AF 36 |
|---|---|---|---|---|
| Water-absorbing component (A)[3] | 1.0-40 | 1.5-30 | 2.0-20 | 3.0-15 |
| Water-absorbing component (B)[6] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

| | AF 37 | AF 38 | AF 39 | AF 40 |
|---|---|---|---|---|
| Water-absorbing component (A)[3] | 1.0-40 | 1.5-30 | 2.0-20 | 3.0-15 |
| Water-absorbing component (B)[6] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D)[8] | 0.0001-15 | 0.001-15 | 0.01-15 | 0.5-15 |
| Cosmetic carrier | Ad 100 | Ad 100 | Ad 100 | Ad 100 |

-continued

|  | AF 41 | AF 42 | AF 43 | AF 44 |
|---|---|---|---|---|
| Water-absorbing component (A)[3] | 1.0-40 | 1.5-30 | 2.0-20 | 3.0-15 |
| Water-absorbing component (B)[6] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D)[8] | 0.0001-15 | 0.001-15 | 0.01-15 | 0.5-15 |
| Cosmetic carrier[9] | Ad 100 | Ad 100 | Ad 100 | Ad 100 |

|  | AF 45 | AF 46 | AF 47 | AF 48 |
|---|---|---|---|---|
| Water-absorbing component (A)[3] | 1.0-40 | 1.5-30 | 2.0-20 | 3.0-15 |
| Water-absorbing component (B)[6] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D)[8] | 0.0001-15 | 0.001-15 | 0.01-15 | 0.5-15 |
| Cosmetic carrier[10] | Ad 100 | Ad 100 | Ad 100 | Ad 100 |

|  | AF 49 | AF 50 | AF 51 | AF 52 |
|---|---|---|---|---|
| Water-absorbing component (A)[11] | 1.0-40 | 1.5-30 | 2.0-20 | 3.0-15 |
| Water-absorbing component (B) | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

|  | AF 53 | AF 54 | AF 55 | AF 56 |
|---|---|---|---|---|
| Water-absorbing component (A)[12] | 1.0-40 | 1.5-30 | 2.0-20 | 3.0-15 |
| Water-absorbing component (B) | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

|  | AF 57 | AF 58 | AF 59 | AF 60 |
|---|---|---|---|---|
| Water-absorbing component (A) | 1.0-40 | 1.5-30 | 2.0-20 | 3.0-15 |
| Water-absorbing component (B)[13] | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

|  | AF 61 | AF 62 | AF 63 | AF 64 |
|---|---|---|---|---|
| Water-absorbing component (A) | 1.0-40 | 1.5-30 | 2.0-20 | 3.0-15 |
| Water-absorbing component (B)[14] | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

|  | AF 65 | AF 66 | AF 67 | AF 68 |
|---|---|---|---|---|
| Water-absorbing component (A)[15] | 1.0-40 | 1.5-30 | 2.0-20 | 3.0-15 |
| Water-absorbing component (B) | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

|  | AF 69 | AF 70 | AF 71 | AF 72 |
|---|---|---|---|---|
| Water-absorbing component (A) | 1.0-40 | 1.5-30 | 2.0-20 | 3.0-15 |
| Water-absorbing component (B)[16] | 1.0-40 | 1.5-30 | 2.0-20 | 2.0-15 |
| Odor-absorbing component (C) | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

|  | AF 73 | AF 74 | AF 75 | AF 76 |
|---|---|---|---|---|
| Water-absorbing component (A)[11] | 1.0-40 | 1.5-30 | 2.0-20 | 3.0-15 |
| Water-absorbing component (B)[13] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

-continued

|  | AF 77 | AF 78 | AF 79 | AF 80 |
|---|---|---|---|---|
| Water-absorbing component (A)[11] | 1.0-40 | 1.5-30 | 2.0-20 | 3.0-15 |
| Water-absorbing component (B)[14] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

|  | AF 81 | AF 82 | AF 83 | AF 84 |
|---|---|---|---|---|
| Water-absorbing component (A)[12] | 1.0-40 | 1.5-30 | 2.0-20 | 3.0-15 |
| Water-absorbing component (B)[13] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

|  | AF 85 | AF 86 | AF 87 | AF 88 |
|---|---|---|---|---|
| Water-absorbing component (A)[12] | 1.0-40 | 1.5-30 | 2.0-20 | 3.0-15 |
| Water-absorbing component (B)[14] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

|  | AF 89 | AF 90 | AF 91 | AF 92 |
|---|---|---|---|---|
| Water-absorbing component (A)[15] | 1.0-40 | 1.5-30 | 2.0-20 | 3.0-15 |
| Water-absorbing component (B)[16] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D) | 0.0001-15 | 0.001-15 | 0.01-15 | 0.5-15 |
| Cosmetic carrier | Ad 100 | Ad 100 | Ad 100 | Ad 100 |

|  | AF 93 | AF 94 | AF 95 | AF 96 |
|---|---|---|---|---|
| Water-absorbing component (A)[11] | 1.0-40 | 1.5-30 | 2.0-20 | 3.0-15 |
| Water-absorbing component (B)[13] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D)[8] | 0.0001-15 | 0.001-15 | 0.01-15 | 0.5-15 |
| Cosmetic carrier[10] | Ad 100 | Ad 100 | Ad 100 | Ad 100 |

|  | AF 97 | AF 98 | AF 99 | AF 100 |
|---|---|---|---|---|
| Water-absorbing component (A)[11] | 1.0-40 | 1.5-30 | 2.0-20 | 3.0-15 |
| Water-absorbing component (B)[14] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D)[8] | 0.0001-15 | 0.001-15 | 0.01-15 | 0.5-15 |
| Cosmetic carrier[10] | Ad 100 | Ad 100 | Ad 100 | Ad 100 |

|  | AF 101 | AF 102 | AF 103 | AF 104 |
|---|---|---|---|---|
| Water-absorbing component (A)[12] | 1.0-40 | 1.5-30 | 2.0-20 | 3.0-15 |
| Water-absorbing component (B)[13] | 1.0-40 | 1.5-30 | 2.0-20 | 2.0-15 |
| Odor-absorbing component (C)[7] | 1.0-40 | 1.5-30 | 2.0-20 | 2.0-15 |
| Deodorant active ingredient (D)[8] | 0.0001-15 | 0.001-15 | 0.01-15 | 0.5-15 |
| Cosmetic carrier[10] | Ad 100 | Ad 100 | Ad 100 | Ad 100 |

|  | AF 105 | AF 106 | AF 107 | AF 108 |
|---|---|---|---|---|
| Water-absorbing component (A)[12] | 1.0-40 | 1.5-30 | 2.0-20 | 3.0-15 |
| Water-absorbing component (B)[14] | 1.0-40 | 1.5-30 | 2.0-20 | 2.0-15 |
| Odor-absorbing component (C)[7] | 1.0-40 | 1.5-30 | 2.0-20 | 2.0-15 |

| | | | | |
|---|---|---|---|---|
| Deodorant active ingredient (D)[8] | 0.0001-15 | 0.001-15 | 0.01-15 | 0.5-15 |
| Cosmetic carrier[10] | Ad 100 | Ad 100 | Ad 100 | Ad 100 |

[1] selected from the group of xanthan gum, gellan gum, cellulose gum, cellulose ethers, linear or crosslinked sodium polyacrylates, alginic acid and its salts, carrageenan and its salts, agar agar, pectins, guar gum, starch ethers, starch esters, locust bean flour, gelatins, succinoglycan, polyvinylpyrrolidone, crosslinked copolymers of acrylamide and acrylic acid, tara gum and mixtures thereof,
[2] strongly swelling water-absorbing component (A) is present in particle form, wherein at least about 30 wt. % of component (A) has an average particle size $D_{50}$ of more than about 10 µm and wherein about 100 wt. % of component (A) has an average particle size $D_{50}$ of less than about 200 µm.
[3] selected from the group of sodium carboxy methyl cellulose or crosslinked copolymers of acrylamide an acrylic acid
[4] selected from the group of celluloses, microcrystalline celluloses, maltodextrin, starch and derivatives thereof, silica, modified silica, talc, clays, hectorites, silicas, perlites, metal oxides, metal hydroxides, metal carbonates, metal oxide hydroxides, metal oxide carbonates, metal hydroxide carbonates, isolated plant constituents and mixtures thereof,
[5] low-swelling water-absorbing component (B) is present in particle form, wherein at least about 30 wt. % of component (B) has an average particle size $D_{50}$ of more than about 10 µm and wherein about 100 wt. % of component (B) has an average particle size $D_{50}$ of less than about 200 µm,
[6] selected from the group of hydrophilic silica, particularly with a BET surface area of from about 250 to about 350 $m^2/g$, or cellulose
[7] selected from the group of cyclodextrins and their derivatives, zeolites, sodium hydrogen carbonate, magnesium hydroxide, magnesium carbonate, magnesium oxide, zinc carbonate, zinc carbonate hydroxide, silica, sodium aluminum silicates, zinc ricinoleate, zinc salts of the L-pyrrolidone carboxylate, sodium silicoaluminates, magnesium calcium silicates, magnesium aluminum silicates, zinc chloride hydroxide, noble metal powders, perlites, metal-organic frameworks (MOFs) and mixtures thereof
[8] selected from phenoxyethanol and/or caprylyl glycol and/or 1,2-hexanediol and/or α-(2-ethylhexyl) glycerol ether and/or benzyl heptanol and/or butyloctanoic acid,
[9] selected from a mixture of a) cyclopentadienyl, b) ethylhexyl palmitate and c1) isopropyl myristate or c2) polydimethylsiloxane having a kinematic viscosity of from about 2 to about 30 cSt,
[10] selected from a mixture of a) cyclopentadienyl, b) ethylhexyl palmitate and c1) isopropyl myristate or c2) polydimethylsiloxane having a kinematic viscosity of from about 2 to about 30 cSt in the weight ratio of from about 12:7:1 to about 8:4:1
[11] sodium carboxymethylcellulose,
[12] crosslinked polymers of acrylamide and acrylic acid,
[13] hydrophilic silica, particularly with a BET surface area of from about 250 to about 350 $m^2/g$,
[14] cellulose,
[15] mixture of sodium carboxymethylcellulose and at least one crosslinked copolymer of acrylamide and acrylic acid,
[16] mixture of hydrophilic silica BET surface area of from about 250 to about 350 $m^2/g$ and cellulose.

The aforementioned particularly preferred embodiments AF1 to AF108 of the compositions achieve a strong minimization of the formation of sweat spots on textiles and a dry, non-greasy skin feeling during and after application of this composition. Furthermore, these embodiments have high storage stability, outstanding deodorizing effect and good product haptics.

The formulation of the composition in a specific dosage form, such as an antiperspirant roll-on, an antiperspirant stick or an antiperspirant gel is preferentially based on the requirements of the intended use. Therefore, depending on the intended use, the compositions can be produced in a solid, semi-solid manner, liquid, dispersed, emulsified, suspended, gel-like, multi-phase or powder form. For the purposes of the present disclosure, the term "liquid" also encompasses any types of solid-state dispersions in liquids. Furthermore, multi-phase compositions used in the context of the present disclosure are understood to mean compositions which have at least 2 different phases with a phase separation and in which the phases are arranged horizontally, in other words one above the other, or vertically, that is to say next to one another. Application of such compositions can take place, for example, as a solid stick, soft solid, cream, roll-on dibenzylidene-alditol-based gel, or loose or compact powder.

Creamy, gel-like, pasty and liquid compositions as contemplated herein can be used, for example, in pump, spray or squeeze dispensers, particularly in multi-chamber pump, multi-chamber spray or multi-changer squeeze dispensers. The packaging can be opaque, transparent or translucent and may contain no propellants.

However, application of the composition preferably takes place by employing a spray device, which contains the anhydrous composition and at least one propellant in a container. Therefore, a second subject of the present disclosure is a cosmetic product comprising
a) at least one anhydrous cosmetic composition and
b) at least one propellant (E).

Cylindrical containers made of metal (aluminum, tinplate, maximum capacity preferably about '1,000 ml), protected and/or shatter-proof glass or plastic (maximum capacity preferably about '220 ml) or shattering glass or plastic (maximum capacity preferably from about 50 to about 400 ml) is a suitable example of a container for such cosmetic products. These containers also contain a valve which aids the release of the cosmetic composition in the form of a mist, smoke, foam, powder, paste or liquid jet.

The anhydrous cosmetic composition is the composition described under the first subject of the present disclosure. Therefore, all embodiments of the anhydrous cosmetic composition of the first subject of the present disclosure also apply mutatis mutandis for preferred embodiments of the cosmetic product. The cosmetic product preferably contains the anhydrous cosmetic composition in certain total amounts. Therefore, advantageous embodiments of this subject of the present disclosure are exemplified in that the cosmetic product containing the at least one anhydrous cosmetic composition in a total amount of from about 5.0 to about 50 wt. %, preferably from about 5.0 to about 25 wt. %, more preferably from about 8.0 to about 20 wt. %, particularly from about 10 to about 15 wt. %, relative to the total weight of the cosmetic product. The total weight of the cosmetic product is understood to mean the total weight of the cosmetic composition and the propellant (E). The weight of the packaging of the cosmetic product, particularly the container with valve, is not factored in.

In the context of this subject of the present disclosure, it has been found to be advantageous if certain compounds are used as the propellant (E). Therefore, it is preferred if the at least one propellant (E) is selected from the group of propane, propene, n-butane, isobutane, isobutene, n-pentane, pentene, isopentane, isopentene, methane, ethane, dimethyl ether, nitrogen, air, oxygen, nitrous oxide, 1,1,1,3-tetrafluoroethane, heptafluoro-n-propane, perfluoroethane, monochlorodifluoromethane, 1,1-difluoroethane, tetrafluoropropene and mixtures thereof. Particularly preferred propellants (E) are propane, n-butane, isobutane and mixtures thereof, particularly a mixture of propane and n-butane in a weight ratio of 15:85.

In order to ensure adequate sprayability of the anhydrous composition, it is advantageous if the cosmetic product contains the at least one propellant (E) in a specific total amount. Therefore, preferred embodiments are exemplified in that the at least one propellant (E) is contained in a total amount of from about 10 to about 95 wt. %, preferably from about 60 to about 95 wt. %, more preferably from about 70 to about 95 wt. %, particularly from about 75 to about 95 wt. %, relative to the total weight of the cosmetic product. The total weight of the cosmetic product is understood to mean the total weight of the cosmetic composition and the propellant (E). The weight of the packaging of the cosmetic product, particularly the container with valve, is not factored in.

Particularly preferred embodiments K1 to K12 of the cosmetic product as contemplated herein are described below (all specifications in wt. %). All cosmetic products below have a total amount of free water of from about 0 to about 1.0 wt. %, particularly from about 0 to about 0.2 wt. %, relative to the total weight of the respective product.

|  | K1 | K2 | K3 | K4 |
|---|---|---|---|---|
| Anhydrous cosmetic composition[1] | 5.0-50 | 5.0-25 | 8.0-20 | 10-15 |
| Propellant (E) | Ad 100 | Ad 100 | Ad 100 | Ad 100 |
|  | K5 | K6 | K7 | K8 |
| Anhydrous cosmetic composition[1] | 5.0-50 | 5.0-25 | 8.0-20 | 10-15 |
| Propellant (E)[2] | Ad 100 | Ad 100 | Ad 100 | Ad 100 |
|  | K9 | K10 | K11 | K12 |
| Anhydrous cosmetic composition[1] | 5.0-50 | 5.0-25 | 8.0-20 | 10-15 |
| Propellant (E)[3] | Ad 100 | Ad 100 | Ad 100 | Ad 100 |

[1] selected from one of the particularly preferred embodiments AF1 to AF108 under the first subject of the present disclosure
[2] selected from the group of propane, propene, n-butane, isobutane, isobutene, n-pentane, pentene, isopentane, isopentene, methane, ethane, dimethylester, nitrogen, air, oxygen, nitrous oxide, 1,1,1,3-tetrafluoroethane, heptafluoro-n-propane, perfluoroethane, monochlorodifluoromethane, 1,1-difluoroethane and tetrafluoropropenes and mixtures thereof
[3] selected from propane, n-butane, isobutane and mixtures thereof The aforementioned cosmetic products K1 to K12 have good sprayability. Moreover, these products do not cause premature clogging of valves and can be sprayed completely. In addition, these products do not have any corrosive properties and have a high storage stability. Application of these products also has the effect of minimizing sweat spots on textiles and an outstanding deodorizing effect. Furthermore, a dry, non-greasy skin feeling is achieved. With regard to other preferred embodiments of the cosmetic product, the statements apply mutatis mutandis to the anhydrous composition.

A third subject of the present disclosure is the use of the anhydrous cosmetic composition or the cosmetic product for reduction of body odor released by perspiration.

Use of the anhydrous composition and/or the cosmetic product achieves an outstanding deodorizing effect based on the combination of components (A) to (D). Without wishing to restrict this in theory, the high water-absorption capacity of the composition or the product results in a reduced growth of bacteria, which converts the sweat into unpleasant-smelling compounds.

With regard to additional preferred embodiments of the use, particularly with regard to the composition and/or product that is used, the statements apply mutatis mutandis to the anhydrous composition and the cosmetic product.

Finally, a fourth subject of the present disclosure is the use of at least one combination of
a) at least one strongly swelling water-absorbing component (A)
b) at least one low-swelling water-absorbing component (B) and
c) at least one odor-absorbing component (C)
to improve the sensory properties of anhydrous deodorant compositions.

The term "combination" in the context of the present disclosure is understood to mean a mixture of the aforementioned components (A) to (C). Furthermore, the term "improvement of sensory properties of anhydrous deodorant composition", is understood to mean, in particular, the improved dry skin feeling that the composition leaves after application on the skin. The deodorant compositions contain at least one of the deodorant active ingredients listed under the first subject of the present disclosure.

Use of the aforementioned components (A) and (B) achieves high water absorption and thus a dry skin feeling without negatively influencing sensory characteristics. This dry skin feeling is further enhanced with the use of component (C).

With regard to additional preferred embodiments of this subject of the present disclosure, particularly with regard to the components (A) to (C) used in this subject, the statements apply mutatis mutandis for the anhydrous cosmetic composition.

The following examples explain the present disclosure without limiting it:

EXAMPLES

Sodium carboxy methyl cellulose and/or a crosslinked copolymer of acrylamide and acrylic acid are used as a strongly swelling water-absorbing component (A) in the following examples. The less-swelling water-absorbing component (B) is preferably a hydrophilic silica, particularly with a BET surface area of from about 250 to about 350 $m^2/g$, and/or cellulose. The particularly preferred odor-absorbing component is selected from the group of cyclodextrines and their derivatives, zeolites, sodium hydrogen carbonate, magnesium hydroxide, magnesium carbonate, magnesium oxide, zinc carbonate, zinc carbonate hydroxide, silica, sodium aluminum silicates, zinc ricinoleate, zinc salts of the L-pyrrolidone carboxylate, sodium silicoaluminates, magnesium calcium silicates, magnesium aluminum silicates, zinc chloride hydroxide, noble metal powders, perlites, metal-organic frameworks (MOFs) and mixtures thereof. Phenoxyethanol and/or caprylyl glycol and/or 1,2-hexanediol and/or α-(2-ethylhexyl) glycerol ether and/or benzyl heptanol and/or butyloctanoic acid are preferably used as deodorant active ingredient (D).

Anhydrous Suspensions (Specifications in Wt. %):

|  | 1.1 | 1.2 | 1.3 | 1.4 | 1.5 | 1.6 |
|---|---|---|---|---|---|---|
| Component (A) | 10 | 5.0 | 7.0 | 7.0 | 8.0 | 8.0 |
| Component (B) | 2.0 | 5.0 | 3.0 | 3.0 | 2.0 | 2.0 |

-continued

|  | | | | | | |
|---|---|---|---|---|---|---|
| Component (C) | 2.0 | 3.0 | 5.0 | 2.0 | 1.0 | 5.0 |
| Deodorant active ingredient (D) | 2.3 | 2.3 | 2.3 | 2.3 | 2.3 | 2.3 |
| Triethyl citrate (D) | 8.0 | 8.0 | 8.0 | 8.0 | 8.0 | 8.0 |
| Ethylhexyl palmitate | 8.0 | 8.0 | 8.0 | 8.0 | 8.0 | 8.0 |
| Isopropyl myristate | — | — | — | — | — | 10 |
| Polydimethylsiloxane (10 cst) | — | — | — | — | 10 | — |
| Disteardimonium hectorite | 3.7 | 3.7 | 3.7 | 3.7 | 3.7 | 3.7 |
| Propylene carbonate | 1.2 | 1.2 | 1.2 | 1.2 | 1.2 | 1.2 |
| Perfume | 6.7 | 6.7 | 6.7 | 6.7 | 6.7 | 6.7 |
| Cyclopentasiloxane | ad 100 | ad 100 | ad 100 | ad 100 | ad 100 | ad 100 |

|  | 1.7 | 1.8 | 1.9 | 1.10 | 1.11 | 1.12 |
|---|---|---|---|---|---|---|
| Sodium carboxy methyl cellulose | 6.0 | 5.0 | — | — | — | 8.0 |
| Silica pearls | 4.0 | — | 2.0 | 4.0 | — | — |
| Cellulose powder | — | 5.0 | — | — | 2.0 | — |
| Perlite | — | — | — | — | — | 2.0 |
| Xanthan | — | — | 8.0 | — | — | — |
| Succinoglycan | — | — | — | 6.0 | — | — |
| Tara gum | — | — | — | — | 8.0 | — |
| Component (C) | 1.0 | 2.0 | 5.0 | 3.0 | 2.0 | 5.0 |
| Deodorant active ingredient (D) | 2.3 | 2.3 | 2.3 | 2.3 | 2.3 | 2.3 |
| Triethyl citrate | 5.0 | 5.0 | 8.0 | 8.0 | 8.0 | 8.0 |
| Ethylhexyl palmitate | — | 10 | 8.0 | 8.0 | 8.0 | 8.0 |
| Isopropyl myristate | 10 | 5.0 | 10 | — | — | 10 |
| Polydimethylsiloxane (10 cst) | 10 | — | — | — | 10 | — |
| Disteardimonium hectorite | 2 | 4 | 3.7 | 3.7 | 3.7 | 3.7 |
| Propylene carbonate | 1.2 | 1.5 | 1.2 | 1.2 | 1.2 | 1.2 |
| Perfume | 6.7 | 3.0 | 6.7 | 6.7 | 6.7 | 6.7 |
| Cyclopentasiloxane | ad 100 | ad 100 | ad 100 | ad 100 | ad 100 | ad 100 |

Formulations 1.1 to 1.12 can be applied in the form of an aerosol spray. For this purpose, from about 10 to about 40 parts of the respective formulation 1.1 to 1.12 are filled in a suitable aerosol container and applied to the skin by employing a suitable spray device with from about 90 to about 60 parts of a suitable propellant selected from propane, n-butane, isobutane or mixtures thereof.

Anhydrous Suspension (Specifications in Wt. %):

|  | 2.1 | 2.2 | 2.3 | 2.4 | 2.5 | 2.6 |
|---|---|---|---|---|---|---|
| Sodium carboxy methyl cellulose | 20 | 5.0 | 7.0 | 7.0 | 8.0 | 8.0 |
| Silica pearls | — | 10 | 3.0 | — | — | 2.0 |
| Cellulose powder | 2.0 | — | — | 3.0 | 2.0 | — |
| Component (C) | 1.0 | 2.0 | 3.0 | 5.0 | 1.0 | 10 |
| Deodorant active ingredient (D) | 2.3 | 0.5 | 1.5 | 1.0 | 1.2 | 0.8 |
| Triethyl citrate (D) | 5.0 | — | 3.0 | — | 1.0 | 4.0 |
| Ethylhexyl palmitate | 20 | 8.0 | 10 | — | 8.0 | 8.0 |
| Isopropyl myristate | — | — | — | — | — | 10 |
| Polydimethylsiloxane (10 cst) | — | — | — | 10 | 15 | 10 |
| Disteardimonium hectorite | 3.7 | 3.0 | 6.0 | 3.7 | 3.7 | 3.7 |
| Propylene carbonate | 1.2 | 1.2 | 3.0 | 1.2 | 1.2 | 1.2 |
| Perfume | 2.0 | 1.0 | 1.5 | 1.0 | 6.7 | 6.7 |
| Cyclopentasiloxane | ad 100 | ad 100 | ad 100 | ad 100 | ad 100 | ad 100 |

Formulations 2.1 to 2.6 can be applied, for example, as a suspension from a roll-on container.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An anhydrous cosmetic composition consisting of:
   a) a strongly swelling water-absorbing component (A) consisting of sodium carboxymethyl cellulose alone or in combination with crosslinked copolymers of acrylamide and acrylic acid, and optionally including one or more additional compounds from the group of xanthan gum, gellan gum, cellulose gum, linear or crosslinked sodium polyacrylates, alginic acid and its salts, carrageenan and its salts, agar agar, pectins, guar gum, starch ethers, starch esters, locust bean flour, gelatins, succinoglycan, polyvinylpyrrolidone, crosslinked copolymers of acrylamide and acrylic acid, tara gum and mixtures thereof;
   b) a low-swelling water-absorbing component (B) consisting of hydrophilic silica or cellulose or a combination thereof;
   c) an odor-absorbing component (C) comprising cyclodextrin;

d) a deodorant active ingredient (D) consisting of phenoxyethanol, caprylyl glycol, 1,2-hexanediol, α-(2-ethylhexyl) glycerol, benzyl heptanol and/or butyloctanoic acid, or a mixture thereof;
e) an anhydrous cosmetic carrier (E); and
optionally one or more additional ingredients selected from the group of: (i) fragrances; (ii) waxes; (iii) emulsifiers and/or surfactants; (iv), chelating agents; (v) polyethylene glycols; (vi) skin-cooling active ingredients; (vii) pH control agents; (viii) skin-care active ingredients, selected from the group consisting of: moisturizers, skin-calming substances, skin-lightening substances, and skin-smoothing substances; (ix) preservatives; and (x) mixtures thereof,
wherein the sodium carboxymethyl cellulose of component (A) consists of a particle form, wherein at least 30 wt. % of the particle form has an average particle size $D_{50}$ of more than 10 micrometers (μm) and wherein 100 wt. % of the particle form has an average particle size $D_{50}$ of less than 200 μm, and
wherein the anhydrous cosmetic composition consists of a mixture of components (A), (B), (C), ingredient (D), cosmetic carrier (E), and optionally the one or more additional ingredients.

2. The anhydrous cosmetic composition according to claim 1 wherein the strongly swelling water-absorbing component (A) is included in a total quantity of from about 1.0 to about 40 wt. %, relative to a total weight of the anhydrous cosmetic composition.

3. The anhydrous cosmetic composition according to claim 1, wherein the low-swelling water-absorbing component (B) is included in a total quantity of from about 1.0 to about 40 wt. %, relative to a total weight of the anhydrous cosmetic composition.

4. The anhydrous cosmetic composition according to claim 1, wherein the anhydrous cosmetic composition has a weight ratio of the strongly swelling water-absorbing component (A) to the low-swelling water-absorbing component (B) of from about 8:2 to about 2:8.

5. A cosmetic product, consisting of:
a) an anhydrous cosmetic composition consisting of:
a strongly swelling water-absorbing component (A) consisting of sodium carboxymethyl cellulose alone or in combination with crosslinked copolymers of acrylamide and acrylic acid, and optionally including one or more additional compounds from the group of xanthan gum, gellan gum, cellulose gum, linear or crosslinked sodium polyacrylates, alginic acid and its salts, carrageenan and its salts, agar agar, pectins, guar gum, starch ethers, starch esters, locust bean flour, gelatins, succinoglycan, polyvinylpyrrolidone, crosslinked copolymers of acrylamide and acrylic acid, tara gum and mixtures thereof;
a low-swelling water-absorbing component (B) consisting of hydrophilic silica or cellulose or a combination thereof;
an odor-absorbing component (C) comprising cyclodextrin;
a deodorant active ingredient (D) consisting of phenoxyethanol, caprylyl glycol, 1,2-hexanediol, α-(2-ethylhexyl) glycerol, benzyl heptanol and/or butyloctanoic acid, or a mixture thereof;
an anhydrous cosmetic carrier (E); and
optionally one or more additional ingredients selected from the group of: (i) fragrances; (ii) waxes; (iii) emulsifiers and/or surfactants; (iv), chelating agents; (v) polyethylene glycols; (vi) skin-cooling active ingredients; (vii) pH control agents; (viii) skin-care active ingredients, selected from the group consisting of: moisturizers, skin-calming substances, skin-lightening substances, and skin-smoothing substances; (ix) preservatives; and (x) mixtures thereof,
wherein the sodium carboxymethyl cellulose of component (A) consists of a particle form, wherein at least 30 wt. % of the particle form has an average particle size $D_{50}$ of more than 10 micrometers (μm) and wherein 100 wt. % of the particle form has an average particle size $D_{50}$ of less than 200 μm, and
wherein the anhydrous cosmetic composition consists of a mixture of components (A), (B), (C), ingredient (D), cosmetic carrier (E), and optionally the one or more additional ingredients; and
b) a propellant (F).

6. The anhydrous cosmetic composition of claim 1 wherein:
the strongly swelling water-absorbing component (A) is included in a total quantity of from about 1.5 to about 30 wt. %, relative to a total weight of the anhydrous cosmetic composition.

7. The anhydrous cosmetic composition of claim 1 wherein:
the strongly swelling water-absorbing component (A) is included in a total quantity of from about 2.0 to about 20 wt. %, relative to a total weight of the anhydrous cosmetic composition.

8. The anhydrous cosmetic composition of claim 1 wherein:
the strongly swelling water-absorbing component (A) is included in a total quantity of from about 3.0 to about 15 wt. %, relative to a total weight of the anhydrous cosmetic composition.

9. The anhydrous cosmetic composition of claim 1 wherein:
the low-swelling water-absorbing component (B) is included in a total quantity of from about 1.5 to about 30 wt. %, relative to a total weight of the anhydrous cosmetic composition.

10. The anhydrous cosmetic composition of claim 1 wherein:
the low-swelling water-absorbing component (B) is included in a total quantity of from about 2.0 to about 20 wt. %, relative to a total weight of the anhydrous cosmetic composition.

11. The anhydrous cosmetic composition of claim 1 wherein:
the low-swelling water-absorbing component (B) is included in a total quantity of from about 2.0 to about 15 wt. %, relative to a total weight of the anhydrous cosmetic composition.

12. The anhydrous cosmetic composition of claim 1 wherein:
the anhydrous cosmetic composition has a weight ratio of the strongly swelling water-absorbing component (A) to the low-swelling water-absorbing component (B) of from about 7:2 to about 2:7.

13. The anhydrous cosmetic composition of claim 1 wherein:
the anhydrous cosmetic composition has a weight ratio of the strongly swelling water-absorbing component (A) to the low-swelling water-absorbing component (B) of from about 7:3 to about 4:6.

14. An anhydrous cosmetic composition consisting of:
a) a strongly swelling water-absorbing component (A) consisting of sodium carboxymethyl cellulose alone or in combination with crosslinked copolymers of acrylamide and acrylic acid, and optionally including one or more additional compounds from the group of xanthan gum, gellan gum, cellulose gum, linear or crosslinked sodium polyacrylates, alginic acid and its salts, carrageenan and its salts, agar agar, pectins, guar gum, starch ethers, starch esters, locust bean flour, gelatins, succinoglycan, polyvinylpyrrolidone, crosslinked copolymers of acrylamide and acrylic acid, tara gum and mixtures thereof;
b) a low-swelling water-absorbing component (B) consisting of hydrophilic silica or cellulose or a combination thereof;
c) an odor-absorbing component (C) comprising cyclodextrin;
d) a deodorant active ingredient (D) consisting of phenoxyethanol, caprylyl glycol, 1,2-hexanediol, α-(2-ethylhexyl) glycerol, benzyl heptanol and/or butyloctanoic acid, or a mixture thereof; and
e) an anhydrous cosmetic carrier (E);
wherein the sodium carboxymethyl cellulose of component (A) consists of a particle form, wherein at least 30 wt. % of the particle form has an average particle size $D_{50}$ of more than 10 micrometers (μm) and wherein 100 wt. % of the particle form has an average particle size $D_{50}$ of less than 200 μm, and
wherein the anhydrous cosmetic composition consists of a mixture of components (A), (B), (C), ingredient (D), and cosmetic carrier (E).

\* \* \* \* \*